United States Patent [19]

Burkett et al.

[11] Patent Number: 5,423,746
[45] Date of Patent: Jun. 13, 1995

[54] METHOD AND APPARATUS FOR INFILTRATION DETECTION DURING ADMINISTRATION OF INTRAVENOUS FLUIDS

[75] Inventors: David H. Burkett, San Diego; David E. Kaplan, Moraga, both of Calif.

[73] Assignee: IMED Corporation, San Diego, Calif.

[21] Appl. No.: 66,679

[22] Filed: May 24, 1993

Related U.S. Application Data

[63] Continuation-in-part of Ser. No. 741,257, Aug. 5, 1991, Pat. No. 5,213,573.

[51] Int. Cl.⁶ .............................................. A61M 31/00
[52] U.S. Cl. ...................................... 604/65; 604/131; 604/67; 128/DIG. 13
[58] Field of Search ........................ 604/19, 21, 27, 28, 604/30, 34, 65, 67, 66, 246; 128/DIG. 13

[56] References Cited

U.S. PATENT DOCUMENTS

| | | | |
|---|---|---|---|
| 4,690,673 | 9/1987 | Bloomquist | 604/67 |
| 4,816,019 | 3/1989 | Kamen | 604/65 |
| 4,836,752 | 6/1989 | Burkett | 604/67 |
| 4,846,792 | 7/1989 | Bobo, Jr. et al. | 604/50 |
| 4,979,940 | 12/1990 | Bobo, Jr. et al. | 604/50 |
| 5,087,245 | 2/1992 | Doan | 604/67 |
| 5,096,385 | 3/1992 | Georgi et al. | 417/18 |

FOREIGN PATENT DOCUMENTS

WO82/0005-90 8/1980 WIPO ..................... 604/34

Primary Examiner—C. Fred Rosenbaum
Assistant Examiner—Perry E. Van Over
Attorney, Agent, or Firm—Nydegger & Associates

[57] ABSTRACT

A method for testing for patency at a venous access site during intravenous infusion of a medical solution includes the steps of occluding an intravenous injection tube upstream from the venous access site and monitoring the time and fluid pressure within the tube while the fluid pressure within the tube is varied by external contact with the tube. An apparatus for practicing the method of the invention includes a housing formed with a tube receiving portion for holding a portion of the tube in contact with an occluder finger, a fluid moving finger and a pressure transducer. The fluid moving finger is adapted to contact the tube so as to achieve a testing base pressure in the fluid, after occlusion by the occluder finger. A sequence of pressure drops are then effected by moving the fluid moving finger in stepped increments. An excessive time interval between a pressure drop and a recovery of fluid pressure back to the testing base pressure is an indication of an infiltration condition or some other obstruction.

28 Claims, 5 Drawing Sheets

METHOD AND APPARATUS FOR INFILTRATION DETECTION DURING ADMINISTRATION OF INTRAVENOUS FLUIDS

CROSS REFERENCE TO RELATED APPLICATIONS

This application is a continuation in part of U.S. patent application Ser. No. 07/741,257 filed Aug. 5, 1991 now U.S. Pat. No. 5,213,573 and entitled "IV Administration Set Infiltration Monitor".

FIELD OF THE INVENTION

The present invention relates generally to intravenous (IV) infusion of medical solutions. More particularly, the present invention relates to methods and apparatus for monitoring the proper operation of an IV infusion procedure. The present invention is particularly, though not exclusively, useful for determining if a medical solution is being infiltrated into the tissue surrounding a venous access site rather than being infused into a patient's blood vessel.

BACKGROUND OF THE INVENTION

Intravenous (IV) infusion therapy is a widespread medical technique in which fluid nutrients or fluid medicaments are infused into the bloodstream of a patient through an IV tube as part of a medical procedure for treatment of the patient. More specifically, an IV administration system for IV infusion includes a fluid source, an IV tube and a venipuncture device inserted through the skin into one of the patient's blood vessels at a venous access site. This establishes a flow path from the fluid source to the blood vessel. The fluid nutrients or medicaments may be pumped from the fluid source through the IV tube or drained by gravity through the IV tube into the patient's bloodstream.

While infusion therapy has proven effective in treating a wide range of maladies, it is not without potential complications. One complication, which is of particular concern, is infiltration of the fluid from the IV set into the patient's tissue. More particularly, it sometimes happens that the medical technician who inserts the needle of the IV tube into the patient may fail to properly insert the needle into a blood vessel and instead the needle is inserted into the tissue which surrounds the blood vessel. This results in the infiltration of the IV fluid into the patient's tissue, rather than passage into the blood vessel.

Infiltration of IV fluid into a patient's tissue can also occur during the course of fluid infusion to a patient even though the IV set was originally established for proper operation. For example, patient motion may cause a needle which was originally properly inserted into a blood vessel to become separated from the vessel or lodge against the wall of the vessel or another obstruction. Moreover, the infusion needle may become clotted or an occlusion may occur in the IV tube upstream of the needle. The following disclosure and claims will be generally couched in terms of an infiltration condition, but the term "infiltration" will be understood to include such conditions as clogging of the needle or occlusion of the tube.

It is unfortunately the case that in many circumstances, infiltration of IV liquids into a patient's tissue can go unnoticed by hospital personnel for relatively lengthy periods. This is because it is not feasible for medical establishments to routinely provide personnel who can continuously monitor each and every IV infusion procedure that the medical establishment undertakes. Such infiltration monitoring procedures are relatively labor intensive and generally require a manual test wherein a venous access device such as a hypodermic syringe needle is placed in fluid communication with the venous access site and a return flow of blood from the vein to the IV tube is initiated.

Such manual techniques are difficult to perform and consequently may be unreliable. As an example, for conducting an infiltration test using a hypodermic syringe, the syringe must first be placed in fluid communication with the IV tube. The tube is then manually pinched while the plunger of the syringe is simultaneously retracted to initiate the return flow of fluid. The absence of blood in the return flow is an indication of infiltration.

This procedure requires a good deal of manual dexterity and experience on the part of the clinician. In addition, due to different syringe sizes and different techniques used for performing an infiltration test, results of the tests may vary. Moreover, relatively high pressures can be generated by the syringe, and these pressures may subject the weakened blood vessel walls to damage and the patient to trauma.

Further, it may often be necessary to infuse a supplemental medicament into the patient during infusion therapy. As an example, the primary infusion may be for maintenance of nutrients, while the supplemental fluid may be an antibiotic, sedative, or a medicament administered in conjunction with chemotherapy. Typically, such a supplemental medicament is administered using the same IV administration set but with a separate hypodermic needle which is connected in flow communication with the IV tube. Using the syringe, the physician or other clinician can infuse a supplemental medicant from the syringe into the patient.

With such a supplemental infusion, as with any other IV administration, it is necessary to monitor for infiltration to ascertain whether the venous access site is patent both before and during the IV infusion of the supplemental medicament. In the past, infiltration has been detected manually by the clinician during the supplemental infusion. Typically this is accomplished by manually pinching or occluding an upstream end of the IV tube and then manipulating the syringe to initiate a return flow of blood from the patient into the IV tube. Often times this procedure must be performed several times during the infusion of the supplemental medicament. Such a procedure, in addition to being difficult to perform, may subject the venous access site to excessive pressures and fluid flow rates. Such high pressures and fluid flow rates may damage the walls of the blood vessel which may be weakened by the venipuncture device.

It is thus desirable to be able to automatically monitor IV infusion procedures to ensure the liquid is being infused into the patient's bloodstream and not into the patient's tissue. Automatic systems for monitoring an infusion procedure for infiltration are known in the art. One such prior art system for automatically detecting infiltration during intravenous infusion is disclosed in U.S. Pat. No. 4,816,019 to Kamen. With this system, a valve is used to close off the IV tube. A piston in fluid communication with the contents of the IV tube is then moved to cause a negative pressure step in the IV tube. If the infusion needle is properly situated in the vein, a quantity of fluid will be drawn into the IV tube and the pressure in the IV tube will return to the pressure prior to the negative pressure step. In an infiltration condition however, the pressure in the IV tube will not return to the pre-step pressure in the same time period. By monitoring the pressure in the IV tube during this procedure an infiltration condition can be detected.

Other infiltration detection systems are also known in the art. Although such automatic infiltration systems may function effectively, there is still some room for improvement in the art. In particular, most of these systems are relatively complicated to operate and may not be portable or easily transported. Others may induce relatively high pressures and flow rates of the medical solution being infused. As previously stated, such high pressures and flow rates may damage the blood vessel and cause patient discomfort. Moreover, the medical solution being infused may be subjected to direct contact and contamination or subjected to excessive agitation by the infiltration detection apparatus. In addition, none of the prior art systems permits an infiltration detection apparatus to be controlled in conjunction with the infusion of a supplemental medical solution into the patient from a secondary source of fluids, such as a syringe.

The present invention is directed to an infiltration detection system which uses relatively low pressures and fluid volumes and in which there is no direct contact with the infusion solution. Additionally, the infiltration detection system of the invention is relatively simple to operate and is reliable and portable. Further, the infiltration detection system of the present invention can be selectively controlled while a hypodermic syringe is used to administer a supplemental medicament. This is accomplished using an infiltration detection apparatus connected to the IV tube of the administration set and a novel pressure sensitive thumb switch which is worn by the clinician to control the infiltration detection apparatus.

Accordingly, it is an object of the present invention to provide a method and apparatus for automatically detecting infiltration during an infusion therapy procedure. Another object of the present invention is to provide a method and apparatus for infiltration detection which requires low fluid pressures and low volumes, and which operates without contacting or substantially agitating the medical solution being infused. It is another object of the present invention to provide a method and apparatus for automatically detecting infiltration during an IV infusion therapy procedure in conjunction with infusion of a supplemental medicament from a hypodermic syringe. It is a further object of the present invention to provide an infiltration detection apparatus having a novel pressure sensitive thumb switch that can be operated in conjunction with a hypodermic syringe coupled to an IV administration set to control the infiltration detection procedure during the infusion of a supplemental medicament. It is yet another object of the present invention to provide an apparatus for infiltration detection that is portable and reliable. Finally it is an object of the present invention to provide a method for infiltration detection that is easy to use and an apparatus that is cost effective to manufacture.

SUMMARY OF THE INVENTION

In accordance with the present invention, a method and apparatus for determining whether a medical solution being intravenously administered has infiltrated into the tissue of a patient are provided. The method includes the steps of occluding the IV tube upstream from a venous access site and initiating a pressure drop within the IV tube, by modifying external contact with the IV tube. In order to ascertain if there is infiltration, the pressure within the IV tube, and a time for the pressure to return to a base testing pressure after the pressure drop, are simultaneously monitored. A time interval between the pressure drop and the return of fluid pressure to the testing base pressure is termed herein as a recovery interval. A recovery interval greater than a predetermined time interval is an indication of an infiltration condition. In accordance with the present invention, a method and apparatus are also provided for administering a supplemental fluid to a patient during IV infusion of a primary fluid, while detecting for an infiltration condition.

The infiltration detecting apparatus is adapted to removably engage a length of IV tube. The IV tube is coupled at one end to a supply of a medical solution to be infused and at an opposite end to a venipuncture device at a venous access site. The venipuncture device may be an infusion needle or a sharpened cannula tip. The infiltration detection apparatus is portable and self contained and includes an internal power supply and a keypad for imputing operational instructions. The infiltration detection apparatus also includes visual displays for displaying equipment condition and site status information, an audible alarm to indicate site status and equipment condition, and a microprocessor and associated circuitry.

The infiltration detection apparatus includes an occluder finger coupled to a stepper motor for occluding the IV tube upstream from the venous access site. A fluid moving finger downstream from the occluder finger is coupled to another stepper motor. The fluid moving finger initially partially occludes the IV tube. For generating a pressure drop, the fluid moving finger is partially withdrawn from the IV tube. This movement allows the IV tube to expand, which drops the pressure in the tube and eventually withdraws a quantity of fluid from the patient. The infiltration detection apparatus also includes a pressure sensitive thumb switch for interrupting the infiltration detection procedure when the switch is pressed, followed by initiation of an infiltration detection check by the apparatus when the thumb switch is released. The thumb switch fits over the clinician's thumb and is sandwiched between the clinician's thumb and the plunger of the hypodermic syringe during the supplemental infusion procedure. The thumb switch is electrically coupled by a cable to the control circuit for the infiltration detection apparatus. Thumb pressure exerted by the clinician on the thumb switch during the supplemental infusion closes the thumb switch and temporarily deactivates the infiltration detection procedure. The thumb switch may then be used to reinitiate an infiltration test on demand by lifting the thumb switch off the syringe plunger.

With this arrangement the clinician may infuse a small quantity of the supplemental fluid into the patient and then immediately test for infiltration by lifting the thumb away from the syringe plunger to release pressure on the thumb switch. This initiates an infiltration detection test. The hypodermic syringe can then be manipulated to infuse another quantity of the supplemental fluid, followed by another infiltration test until the contents of the syringe are completely discharged as desired.

During a test sequence, the fluid pressure during a pressure drop and a subsequent pressure recovery interval are measured using a pressure transducer in contact with the exterior of the IV tube. Using the microprocessor, the fluid pressures and times during the pressure drop and the subsequent recovery interval are monitored during a selected number of test steps, for example, ten steps. This data is used to evaluate the patency of the IV tube at the venous access site and to ascertain the occurrence of an infiltration condition.

Initially, a positive pressure exists in the IV tube by virtue of the operating pressure of the IV administration set, and the fluid moving finger is set to partially occlude the IV tube. A test sequence begins by moving the occluder finger to completely occlude the IV tube. The fluid pressure in the IV tube downstream of the occluder finger is then allowed to stabilize. A pressure of 0.5 psig below the stabilized pressure is then calculated. The fluid moving finger is then partially withdrawn to achieve a testing base pressure within the IV tube that is about 0.5 psig below the stabilized pressure.

Once the testing base pressure is reached, the fluid moving finger is additionally withdrawn incrementally, allowing the IV tube to expand, creating a pressure drop from the testing base pressure, for withdrawing fluid. Fluid is then withdrawn from the patient because of this pressure drop, and the pressure in the IV tube returns to the testing base pressure during this recovery interval. The pressure drop is generated by the natural resiliency of the IV tube, which causes it to expand. Pressure recovery is caused by flow of fluid into the tube from the patient. Following this pressure drop and recovery to testing base pressure, this test cycle is repeated through a selected number of test steps, for example, ten steps. Each step of the test sequence, as well as the stabilizing and testing base pressure steps of the test, are timed. Test sequences can be automatically repeated at selected frequencies, for example, one sequence every 5 minutes.

The microprocessor determines whether infiltration has occurred by evaluating the pressure in the IV tube as a function of time during the pressure drop and subsequent recovery interval, as well as the time elapsed over a complete test sequence. For instance, if there is no infiltration, the time for a pressure drop interval and the time for a subsequent recovery interval during a single test step will both be comparatively short, and the time for completion of a test sequence of a given number of steps will be within a predetermined limit. If there is infiltration, on the other hand, the time for a recovery interval will be substantially greater than the time for a pressure drop interval. In general, this is because a fluid can not be as easily withdrawn from infiltrated tissue as from a blood vessel. An obstruction in the needle at the venous access site or a downstream occlusion in the IV tube will provide the same result and may prevent the pressure in the IV tube from returning to the testing base pressure after a pressure drop. Additionally, if the pressure in the IV tube does not stabilize within a predetermined time period after initial occlusion of the IV tube, or if a predetermined testing base pressure is not reached within a predetermined number of motor steps or before a predetermined volume of fluid is withdrawn, then a system malfunction may exist.

The method of the invention may also be used during the infusion of fluids by using an IV administration set for infusion of a primary fluid, and using a hypodermic syringe connected to the IV administration set for infusion of supplemental fluid.

This method, generally stated, includes the steps of connecting a hypodermic syringe in fluid communication with an IV tube of an existing IV administration set, interrupting the infiltration detection procedure while infusing a quantity of a supplemental fluid from the hypodermic syringe into the IV tube, immediately thereafter testing for infiltration, and then infusing another quantity of the supplemental fluid from the syringe until the syringe is emptied as desired, followed by returning to the automatic repetition of infiltration detection test sequences.

Under normal operation, the apparatus will be programmed to automatically repeat the test sequence after a selected time lapse, for example, 5 minutes. This will continue until stopped, either by the operator, equipment malfunction, or the occurrence of an alarm condition where appropriate. If a given automatically initiated test sequence senses an alarm condition, the test frequency can be programmed to automatically increase, for example, to one sequence every minute. The first occurrence of an alarm condition during automatic testing might give one type of alarm indication, while repeated alarm conditions sensed at the increased testing frequency might give a second, more urgent type of alarm indication. Further, it is optional to provide for the performance of a test sequence on demand at the device or by use of the syringe thumb switch. If such a test on demand results in an alarm condition, it might be desirable to program the apparatus to give the more urgent type of alarm indication.

The results of the test can be displayed visually or audibly. As an example, a green light may be used to indicate patency at the venous access site, a yellow light may be used to indicate the first occurrence of an infiltration or obstruction condition which may be transitory, and a red light may be used to indicate that a selected number of consecutive test sequences have resulted in alarm conditions, indicating a sustained infiltration or obstruction condition. A red light may also be used to indicate an alarm result given by a test on demand. Audible signals may also be used to notify the operator of different levels of urgency in the alarm conditions.

The novel features of this invention, as well as the invention itself, both as to its structure and its operation, will be best understood from the accompanying drawings, taken in conjunction with the accompanying description, in which similar reference characters refer to similar parts, and in which:

DESCRIPTION OF PREFERRED EMBODIMENTS

Figure 1:
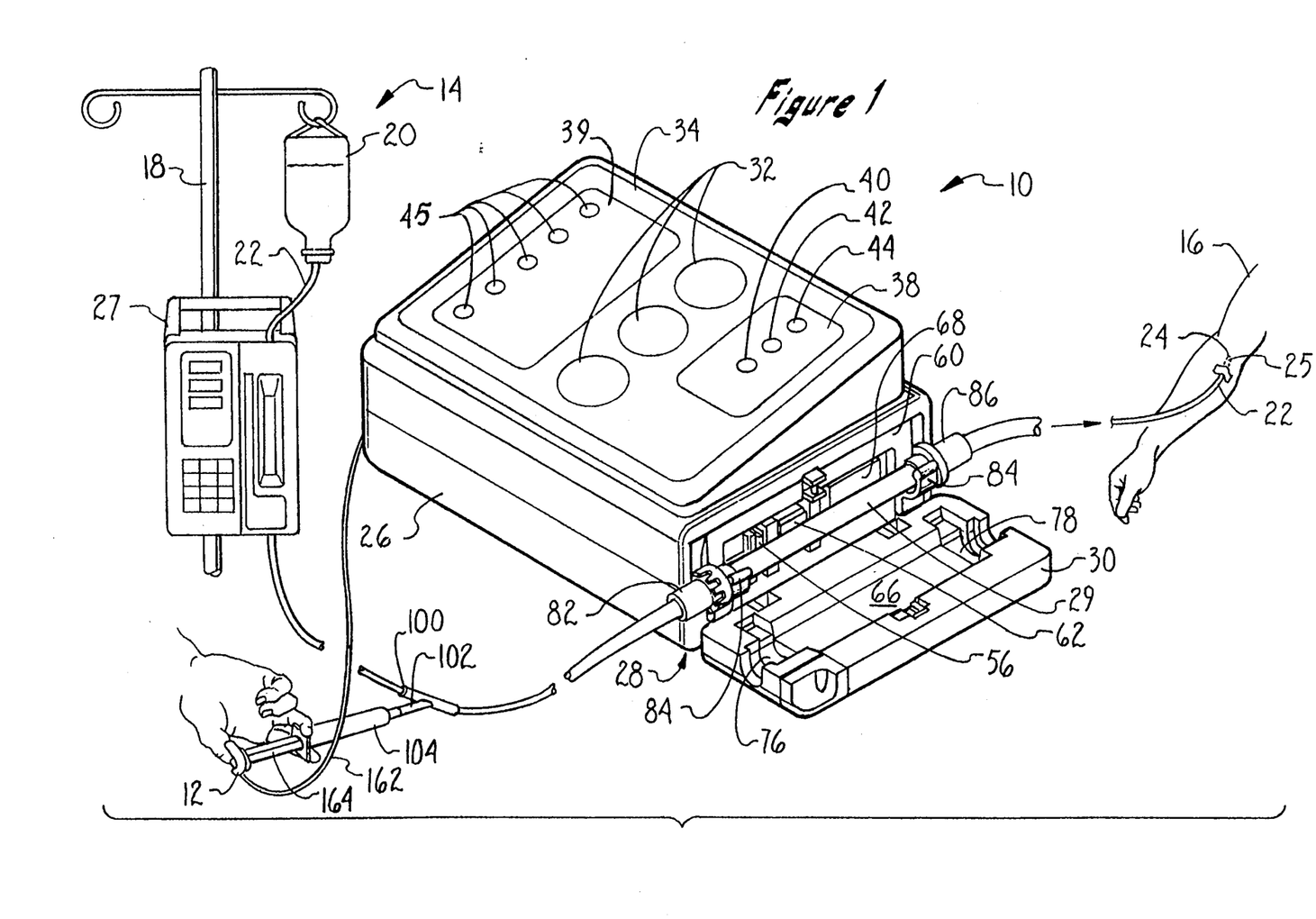
FIG. 1 is a perspective view of an IV infiltration detection apparatus constructed in accordance with the invention and seen in its intended environment.

Referring initially to FIG. 1 an infiltration detection apparatus constructed in accordance with the invention is shown and generally designated as 10. The infiltration detection apparatus 10 is shown in use in an infusion system 14 for infusing a medical solution into a patient 16. The infusion system 14 includes an IV stand 18 on which is mounted a supply reservoir 20 of the primary medical solution. Also shown is optional pressure sensitive thumb switch 12.

An IV line in the form of a resilient IV tube 22 is connected at a distal end in fluid communication with the supply reservoir 20. The IV tube 22 is connected at a proximal end to a venipuncture device 24, such as a hollow needle or sharpened cannula, that is inserted into a vein of the patient 16 at a venous access site 25 in fluid communication with the vein. A pumping device 27, such as a peristaltic pump, is also mounted to the IV stand 18 for positively moving the medical solution through the infusion system 14. By way of example, such a pump may be a peristaltic pump of the type marketed by IMED Corporation under the trade names "PC-1" and "PC-2". Alternately any other suitable mechanism may be used for generating pressure in the IV tube 22 or the medical solution may flow by gravity from the supply reservoir 20 and through the IV tube 22 to the patient.

Figure 7:
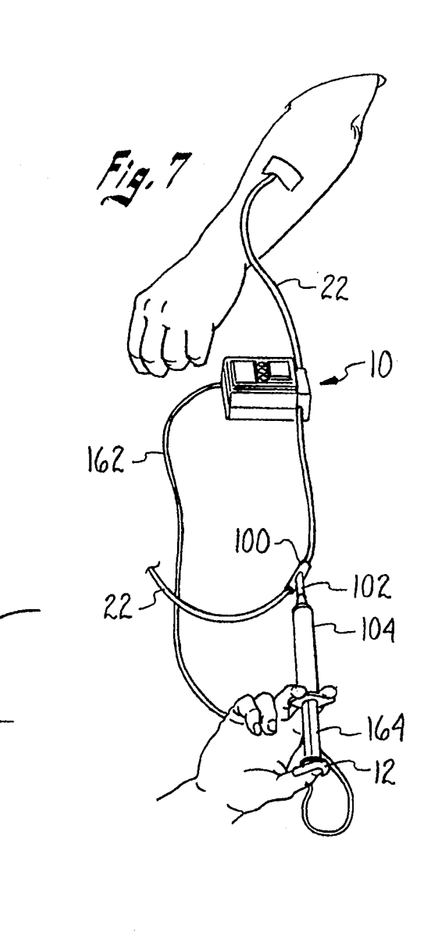
FIG. 7 is a perspective view of an infiltration detection device constructed in accordance with the invention shown in use during the infusion of a supplemental medicament.

As shown in FIGS. 1 and 7, if infusion of a supplemental fluid is desired, a syringe 104 can be inserted into injection site 102 of y-section 100. Thumb switch 12 is placed between the operator's thumb and plunger 164. Switch 12 is electrically connected to infiltration detection apparatus 10 by cable 162.

The infiltration detection apparatus 10 is portable and self contained and is adapted to be placed on a support surface such as a work table (not shown) that is located in close proximity to the patient 16. The infiltration detection apparatus 10 includes a housing 26 formed as a generally rectangular shaped hollow enclosed structure. Most of the individual components of the infiltration detection apparatus 10 including a battery pack 46 (FIG. 2) and a microprocessor 36 (FIG. 2) are mounted within the housing 26.

Externally, the housing 26 includes an IV tube receiving portion 28, with a hinged door 30 formed on a side portion thereof, for receiving a test section 29 of the IV tube 22. In addition, externally, the housing 26 includes a keypad portion 34 having a plurality of keys 32 for imputing instructions into the microprocessor 36 (FIG. 2) of the infiltration detection apparatus 10.

Additionally, the external surface of the housing 26 includes a site status display portion 38 on which a plurality of visual displays are mounted. In an illustrative embodiment the visual displays include a green light 40, a yellow light 42 and a red light 44. The green light 40 indicates an unobstructed venous access site 25. The yellow light 42 indicates an obstruction or infiltration result from a single test sequence during automatic testing. The red light 44 indicates an obstruction or infiltration result from a test sequence performed on demand or from a selected number of consecutive automated sequences. Equipment condition display portion 39 includes a plurality of visual display lights 45, which can indicate equipment conditions such as test in progress, thumb switch activated, pause in test procedure, low battery, or help needed.

Figure 2:
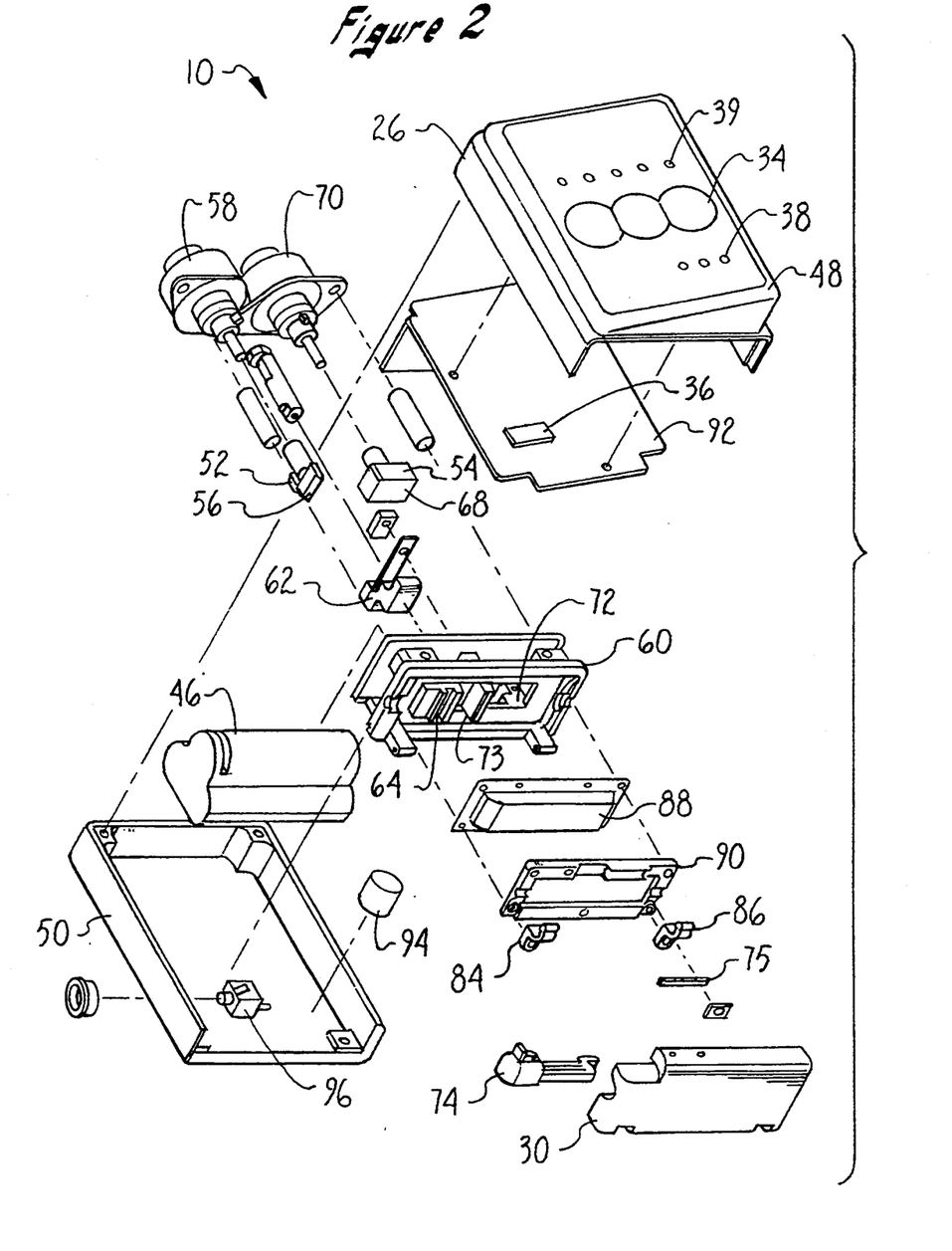
FIG. 2 is an exploded perspective view showing the assembly of the IV infiltration detection apparatus shown in FIG. 1.

Referring now to FIG. 2, the assembly of the infiltration detection apparatus 10 is shown in an exploded view. The housing 26 includes an upper portion 48 and a mating nestable lower portion 50. The housing 26 may be constructed of a sturdy cleanable material such as molded plastic. The upper portion 48 of the housing 26 is removably attached to the lower portion 50 of the housing 26 using suitable fasteners (not shown). This construction allows access to and assembly of the individual components of the infiltration detection apparatus 10 within the housing 26.

A main plate member 60 is mounted within the housing 26 for mounting various components of the infiltration detection apparatus 10 located within the housing 26. The main plate member 60 is shaped substantially as shown in FIG. 2 and contains various openings for the different components of the infiltration detection apparatus 10.

The infiltration detection apparatus includes an occluder finger 52 and a fluid moving finger 54 mounted within the housing 26, extending through the main plate member 60. The occluder finger 52 is mounted for reciprocal movement by a stepper motor 58 which is controlled by the microprocessor 36. The occluder finger 52 is adapted to contact the outside of the test section 29 of the IV tube 22 held within the IV tube receiving portion 28 of the housing 26 to pinch close or occlude the IV tube 22.

The occluder finger 52 has a relatively narrow tip portion 56 for contacting the IV tube 22. The occluder stepper motor 58 moves the occluder finger 52 in a forward or reverse direction as required with respect to the IV tube 22. The main plate member 60 of the housing 26 includes an elongated opening 64 for the tip portion 56 of the occluder finger 52.

For occluding the IV tube 22, the occluder finger 52 is moved forward by the occluder stepper motor 58 such that a portion of the test section 29 (FIG. 1) of the IV tube 22 is pinched closed. As shown in FIG. 1 the housing door 30 is formed with a flat platen portion 66 for supporting the test section 29 of IV tubing 22 for pinching by the occluder finger 52.

The fluid moving finger 54 is mounted for reciprocal movement by a stepper motor 70 controlled by the microprocessor 36. The fluid moving finger 54 is adapted to extend through opening 72 in main plate 60 to contact the outside of the test section 29 of the IV tube 22 to vary the fluid pressure within the IV tube 22. Specifically, face 68 of the fluid moving finger 54 is initially positioned to partially occlude the test section 29 of the IV tube 22 at the time the IV tube is loaded into the infiltration detection apparatus 10. Incrementally withdrawing the fluid moving finger 54 away from the IV tube 22 will allow the IV tube 22 to expand as a result of its natural resiliency, creating a pressure drop within the IV tube 22. A pressure transducer 62 is mounted to extend through opening 73 of the main plate member 60 of the housing 26 for contacting the outside wall of the IV tube 22 to measure the pressure within the IV tube 22.

The components involved can be structured and operated to move quantities of fluid on the order of one (1) microliter or less. The pressure transducer 62 is adapted to detect the pressure within the IV tube 22. The pressure transducer 62 is of a type that does not require an entry site into the IV tube 22 in order to measure the fluid pressure inside the IV tube 22. In a preferred embodiment, the pressure transducer 62 may incorporate a pressure sensing strain beam (not shown). Such a transducer 62 also incorporates a strain gauge (not shown) which may be piezoelectric, that is mounted on the strain beam. The strain beam is connected to a pressure sensing arm that contacts the outside wall of the IV tube 22. Force exerted on the pressure sensing arm, caused by changes of fluid pressure within the IV tube 22 can be detected by the strain gauge to generate an electrical signal representative of the fluid pressure. This signal is sent to the microprocessor 36. Such an arrangement is more fully described in the parent application, Ser. No. 07/741,257, filed Aug. 5, 1991, which is incorporated herein by reference.

Still referring to FIG. 2, further details of the construction of the infiltration detection apparatus 10 will be described. The door 30 for the IV tube receiving portion 28 is hingedly mounted to the lower portion 50 of the housing 26. A latch mechanism 74 is attached to the door 30 for latching the door 30 in a closed position. The latch mechanism is biased by a spring member 75.

Referring now to. FIG. 1, the door 30 includes the platen portion 66 and molded cavities 76, 78 on either end for retaining fitments 82, 86 that are attached to either side of the test section 29 of the IV tube 22. The IV tube retaining portion 28 also includes clips 84 removably attached to the main plate member 60 for initially loading and holding the test section 29 of the IV tube 22. The test section 29 can thus be loaded into the IV tube retaining portion 28 of the housing 26 and retained by the clips 84. The IV tube retaining portion 28 is sized such that with the door 30 closed the test section 29 is initially partially occluded by contact with the contact face 68 of the fluid moving finger 54. In addition, the test section 29 of the IV tube 22 is in contact with the pressure transducer 62.

Referring again to FIG. 2, the infiltration detection apparatus 10 can also include a seal member 88, not shown in FIG. 1 for the sake of clarity, sized and shaped to cover main plate member 60 of the housing 26. The seal member 88 may be formed of a thin flexible material such as polyurethane that seals the openings 64, 72, 73 in the main plate member 60 yet allows the occluder finger 52, the pressure transducer 62, and the fluid moving finger 54 to interact with the test section 29 of the IV tube 22. A bezel 90 attaches the seal 88 to the main plate member 60 of the housing 26.

The infiltration detection apparatus 10 also includes an electrical control circuit for controlling the operation of the infiltration detection apparatus under direction of the microprocessor 36. A circuit board 92 is mounted within the housing 26 for mounting various electrical components of the electrical control circuit including the microprocessor 36. Specifically, the control circuit operatively connects the microprocessor 36 with the stepper motors 58, 70 for operating the occluder finger 52 and fluid moving finger 54, respectively. In addition, the control circuit operatively connects the microprocessor 36 with the pressure transducer 62, the keypads 32 (FIG. 1), and the visual display lights 40, 42, 44, 45 (FIG. 1). The control circuit also includes the electrical components for electrically connecting the battery pack 46. Moreover, the control circuit includes an audible alarm 94. The electrical control circuit also includes a thumb switch jack 96 that can be used to attach the thumb switch 12 to the infiltration detection apparatus 10 via cable 162. The thumb switch 12 functions to deactivate the testing procedure upon application of thumb pressure to the syringe plunger during infusion of a supplemental fluid medicament into the IV tube 22 using a hypodermic syringe, and to immediately initiate a test sequence upon release of thumb pressure.

OPERATION

Figure 3:
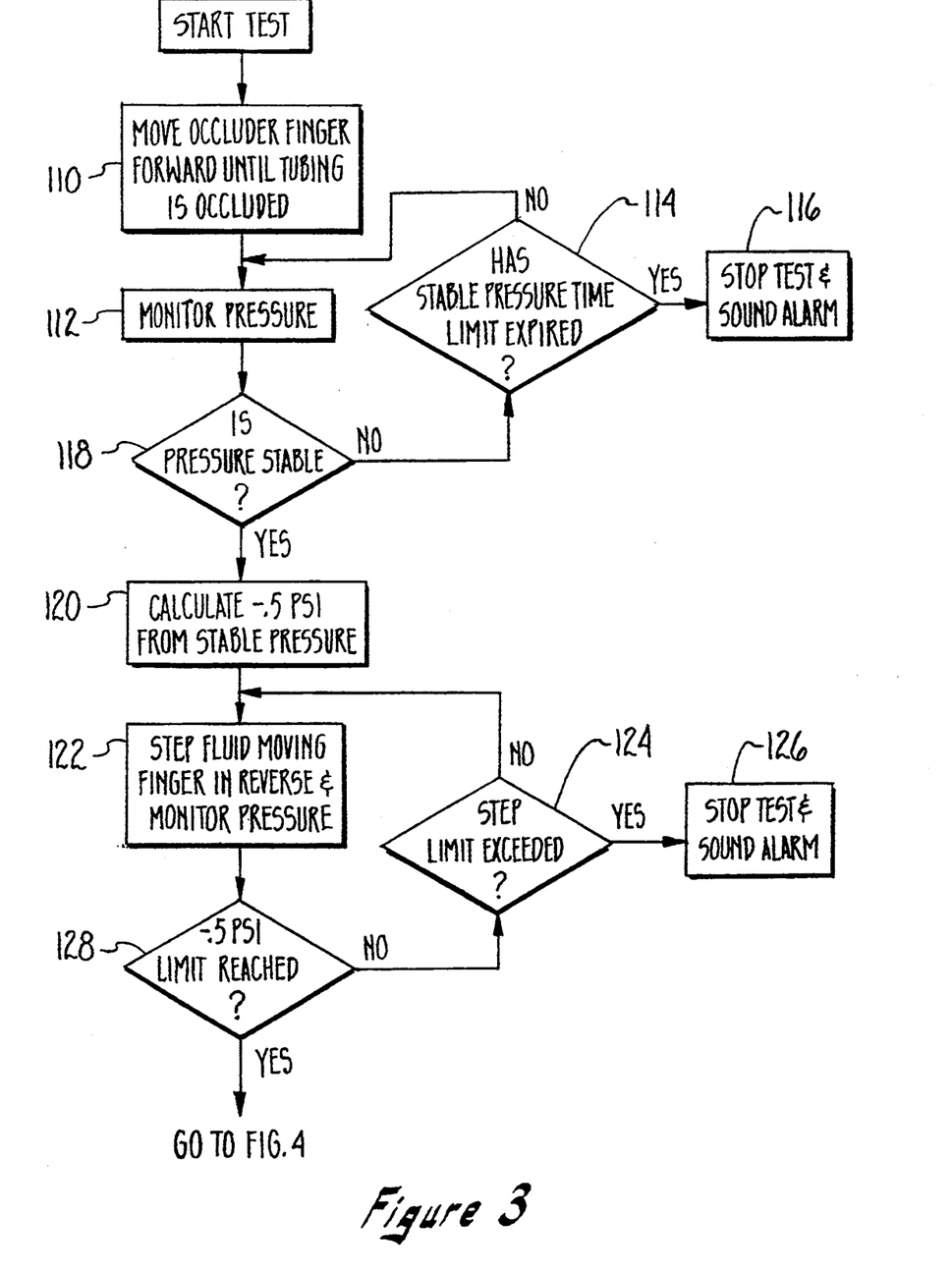
FIG. 3 is a flow diagram of the steps involved in performing an infiltration test in accordance with the method of the invention.
Figure 4:
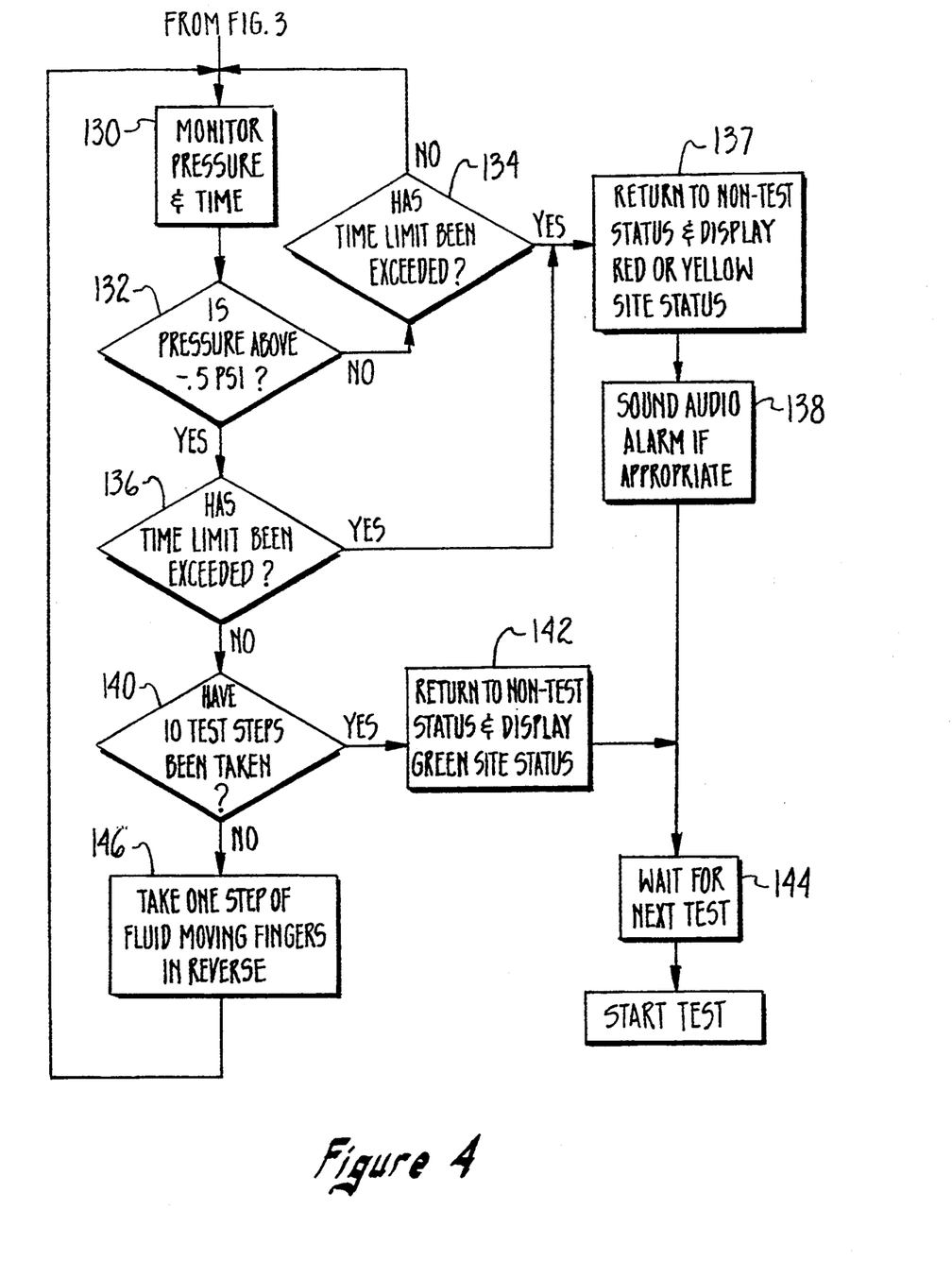
FIG. 4 is a continuation of the flow diagram shown in FIG. 3.

With reference to FIGS. 3 and 4, the infiltration detection apparatus 10 is adapted to perform an infiltration test that includes the following sequence of steps.

1. To start the test sequence the occluder finger 52 is moved forward to occlude the IV tube 22, step 110.

2. During the test, the pressure in the IV tube 22 is monitored, by the pressure transducer 62 and microprocessor 36, step 112. While IV tube 22 is occluded, the pressure in the IV tube 22 is allowed to stabilize. This sequence is timed. If the pressure does not stabilize, decision step 118, within a predetermined time period, decision step 114, this is indicative of a system malfunction. Accordingly, the test is stopped and an alarm is initiated, step 116.

3. If the pressure stabilizes, decision step 118, the microprocessor 36 calculates a testing base pressure that is 0.5 psi below the stabilized pressure, step 120.

4. The fluid moving finger 54 is then partially withdrawn to drop the pressure in the IV tube 22 to the testing base pressure, step 122. If this testing base pressure cannot be reached, decision step 128, within a predetermined number of motor steps or volume of fluid withdrawn, decision step 124, this is indicative of a system malfunction. Accordingly the test is stopped and an alarm is initiated, step 126.

5. If the testing base pressure is reached, step 128, an incremental test sequence is initiated. This test sequence is shown in FIG. 4. Simply stated, this incremental test sequence comprises additional incremental withdrawals of the fluid moving finger 54 to expand the IV tube 22 to initiate a series of pressure drops and withdraw fluid. The time it takes the pressure to return to the testing base pressure, or the recovery interval, is monitored by the pressure transducer 62, and the sequence includes a selected number of steps, such as 10. If the pressure does not return to the testing base pressure within a predetermined time period for a given interval, or if a given test sequence of 10 steps takes longer than a predetermined time period, then an infiltration condition may exist. Some applications, such as neonatal care, will require a modification in the analysis of the test sequence, in order to determine whether an alarm condition truly exists. This is because in such applications, the time for pressure recovery will be extended because of the small size of the cannula, even if patency exists at the venous access site. Therefore, if a given test sequence time limit is exceeded, the microprocessor can be programmed to determine whether at least a selected reduced number of intervals, such as 4, were completed during the sequence, and whether all of the test intervals performed before expiration of the time limit were substantially equal. If both of these conditions are met, the microprocessor can be programmed to indicate patency at the venous access site.

6. During the incremental testing procedure, pressure and time are continuously monitored, step 130 as seen in FIG. 4. If the pressure does not rise during a recovery interval to a level at or above the testing base pressure, decision step 132, within a predetermined recovery interval time limit, decision step 134, then a red or yellow site status light is displayed, step 137, and if appropriate an audible alarm is sounded, step 138. If the pressure does rise during a recovery interval to the testing base pressure, decision step 132, but a predetermined test sequence time limit, for example, 2 seconds, has been exceeded, decision step 136, then appropriate visible and audible displays are initiated as described above. The predetermined recovery interval time limit and the predetermined test sequence time limit can be the same, or they can be different. If an infiltration condition is sensed during a test sequence initiated on demand by the operator, this will result in display of a red light 44 and sounding of a first type of audible alarm, such as 2 beeps. If an infiltration condition is sensed during an automatically initiated test sequence, this will result in display of a yellow light 42 and sounding of 2 beeps as above, accompanied by an automatic increase in the test sequence frequency, such as from one every 5 minutes to one every minute. If a selected number, such as 5, of these more frequent automatic sequences result in infiltration indications, this will result in display of a red light 44 and sounding of a second type of audible alarm, such as continuous beeping.

7. If the pressure does rise to the testing base pressure during a recovery interval, decision step 132, and the test sequence time limit has not been exceeded, decision step 136, and ten test steps have been taken, decision step 140, the infiltration apparatus is returned to a non test status. A green site status is displayed, step 142, and the next test is awaited, step 144. Prior to the next testing sequence the fluid moving finger 54 is advanced forward to its original position.

8. If ten test steps have not been taken as determined in decision step 140, then one additional incremental withdrawal of the fluid moving finger 54 is made, step 146, and step 130 is repeated.

Figure 5:
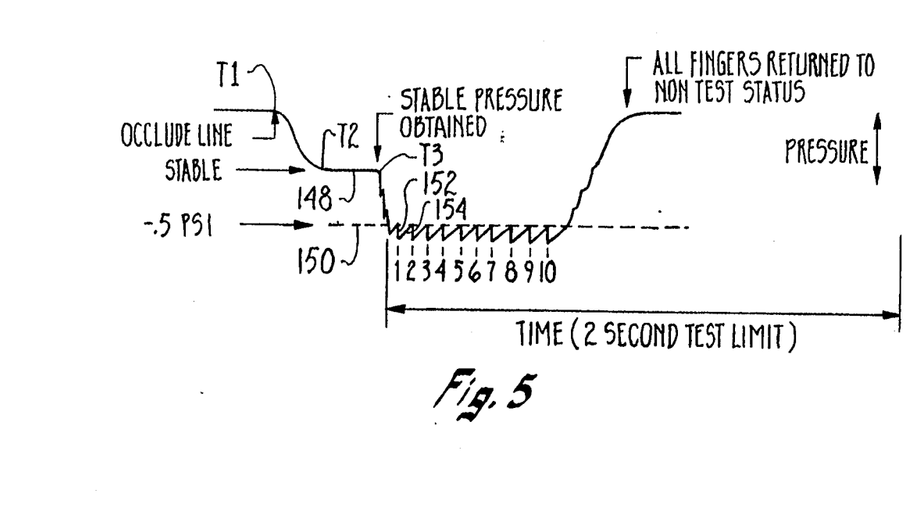
FIG. 5 is a schematic diagram showing pressure as a function of time during an infiltration test conducted in accordance with the invention and in which a venous access site of the IV tube is patent.
Figure 6:
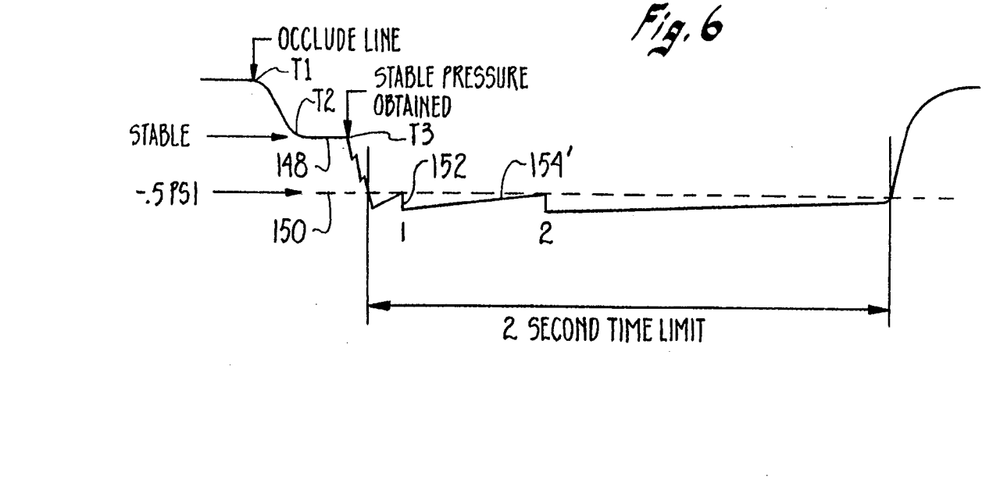
FIG. 6 is a schematic diagram showing pressure as a function of time during an infiltration test conducted in accordance with the invention and in which an IV line is in a condition of infiltration.

Referring now to FIGS. 5 and 6, this testing sequence is shown schematically in a pressure vs. time format. FIG. 5 represents a test sequence in which no infiltration or occlusion condition is detected. FIG. 6 represents a test sequence in which infiltration or an occlusion is detected. With reference to FIG. 5, at time T1 the IV tube 22 is occluded by the occluder finger 52. The pressure in the IV tube 22 drops to a stable pressure 148 at time T2. The microprocessor 36 then calculates a testing pressure that is 0.5 psi below the stable pressure 148. At time T3, the fluid moving finger 54 is partially withdrawn from the IV tube to lower the pressure to the testing base pressure 150. Ten test steps, each comprising a pressure drop followed by a pressure rise or pressure recovery interval, are then taken (steps 1–10). Each pressure drop is initiated by partially withdrawing the fluid moving finger 54 and allowing the IV tube to expand. This drops the pressure in the IV tube 22 by a predetermined amount. The pressure is then allowed to rise back or return to the testing base pressure 150 by the flow of fluid out of the patient and into the IV tube. Once the testing base pressure 150 is reached or exceeded, the negative pressure step is repeated. This incremental pressure step is repeated a total of ten times, or until a predetermined time limit is reached.

During each test step, the pressure drops almost instantaneously once the fluid moving finger 54 is withdrawn. This is represented by the vertical portion 152 of the pressure curve during a test step (i.e step 1). The pressure then rises back to the testing pressure 150 in almost the same time increment as indicated by the sloping portion 154 of the test step. This is because with the IV tube 22 patent at the venous access site, the small quantity of fluid required to restore pressure in the IV tube will flow into the tube very quickly from the blood vessel, and the pressure will return to the testing base pressure 150.

Compare the normal situation shown in FIG. 5 to an abnormal or infiltration condition as noted in FIG. 6. With an infiltration or occlusion condition, the quantity of fluid necessary to restore pressure will not flow out of the patient in as short a period of time as with a patent venous access site. In other words, the infiltration, clot, occlusion, or other obstruction will prevent the subsequent return to the testing base pressure from occurring as quickly. The sloping pressure rise portion 154' of each test step will thus continue over a much larger time increment. If a test sequence time limit, such as 2 seconds, or a recovery interval time limit is reached, then an occlusion or infiltration condition has been demonstrated.

Thus the invention provides a method and apparatus for continuously and automatically testing for infiltration during an IV infusion procedure. While the particular Method and Apparatus for Infiltration Detection During IV Administration as herein shown and disclosed in detail are fully capable of obtaining the objects and providing the advantages herein before stated, it is to be understood that they are merely illustrative of the presently preferred embodiments of the invention and that no limitations are intended to the details of construction or design herein shown other than as described in the appended claims.

We claim:

1. An apparatus for detecting the presence of an obstruction or infiltration of a fluid being delivered through an intravenous tube to a patient, comprising:

occlusion means for occluding an intravenous tube at a first location;

fluid moving means for subjecting the fluid downstream of said first location to a pressure drop below a first pressure level;

pressure monitoring means in contact with an exterior surface of the tube for monitoring fluid pressure within the tube downstream of said first location;

processing means in communication with said occlusion means, said fluid moving means, and said pressure monitoring means, for controlling said occlusion means to occlude the tube, for controlling said fluid moving means to subject the fluid to said pressure drop, for measuring a recovery time interval required for the pressure in the tube to recover to said first pressure level, and for comparing said recovery time interval with a predetermined time interval; and display means connected to said processing means for indicating the results of said comparison.

2. The apparatus as recited in claim 1, wherein said occlusion means comprises an occlusion finger for contacting and occluding the tube.

3. The apparatus as recited in claim 2, wherein said occlusion finger pinches the tube against a platen.

4. The apparatus as recited in claim 1, wherein said fluid moving means comprises a fluid moving finger for partially occluding the tube and adapted to be incrementally withdrawn from the tube a predetermined distance to initiate said pressure drop.

5. The apparatus as recited in claim 1, wherein said fluid moving means is adapted to initiate a plurality of pressure drops in a predetermined time period.

6. The apparatus as recited in claim 1, wherein said fluid moving means is adapted to achieve said first pressure level as a testing base pressure that is a selected amount below a stable pressure existing in the tube after occlusion by said occlusion means.

7. The apparatus as recited in claim 1, wherein said pressure monitoring means comprises a pressure transducer.

8. The apparatus as recited in claim 1, wherein said display means comprises an audible alarm.

9. The apparatus as recited in claim 1, wherein said display means comprises a display light.

10. The apparatus as recited in claim 1, further comprising switching means for controlling operation of said apparatus responsive to introduction of a supplemental fluid into the tube.

11. The apparatus as recited in claim 10, wherein the control exercised by said switching means is interruption of the operation of said apparatus during introduction of the supplemental fluid.

12. The apparatus as recited in claim 10, wherein the control exercised by said switching means is initiation of operation of said occlusion means, said fluid moving means, said pressure monitoring means, and said processing means upon cessation of introduction of the supplemental fluid.

13. An infiltration detection apparatus for monitoring an intravenous infusion procedure in which a fluid is infused into a patient using a tube in fluid communication with a blood vessel of the patient, comprising;

a housing formed with a tube receiving portion for receiving and retaining a portion of an intravenous tube;

an occluder finger reciprocally mounted at a first location within said housing for movement by a first stepper motor to occlude the tube held in said tube receiving portion;

a fluid moving finger mounted downstream of said first location in external contact with the tube within said housing, adapted for reciprocal movement by a second stepper motor, to achieve a pressure drop in the tube to a testing base pressure and to achieve a subsequent pressure drop in the tube by movement away from the tube;

a pressure transducer mounted within said housing in contact with the tube for monitoring the pressure of the fluid within the tube downstream of said first location;

a control circuit mounted within said housing, including a microprocessor electrically connected to said pressure transducer and to said first and second stepper motors, with said microprocessor adapted to control said occluder finger to occlude the tube and to control said fluid moving finger to achieve said testing base pressure and to initiate said subsequent pressure drop in the tube, with said microprocessor adapted to time a period for the pressure in the tube to return to said testing base pressure after said subsequent pressure drop, and with said microprocessor adapted to compare said time period with a predetermined time period; and display means connected to said control circuit for indicating the results of said comparison of said time periods.

14. The apparatus as recited in claim 13, wherein said microprocessor is adapted to time an interval for achieving a stable pressure in the tube after occlusion by said occluder finger.

15. The apparatus as recited in claim 13, wherein said microprocessor is adapted to time an interval for achieving said testing base pressure.

16. The apparatus as recited in claim 13, wherein said display means includes an audible alarm.

17. The apparatus as recited in claim 13, wherein said display means includes a display light.

18. The apparatus as recited in claim 13, wherein said tube receiving means includes a door mounted to said housing for loading the tube in a position in contact with said fluid moving finger and said pressure transducer.

19. The apparatus as recited in claim 13, wherein said fluid moving finger is adapted to achieve said testing base pressure in the tube about 0.5 psi below a stable pressure remaining in the tube after occlusion by said occluder finger.

20. The apparatus as recited in claim 13, further comprising a switch for controlling operation of said apparatus responsive to introduction of a supplemental fluid into said tube.

21. The apparatus as recited in claim 20, wherein the control exercised by said switch is interruption of the operation of said apparatus during introduction of the supplemental fluid, 22. The apparatus as recited in claim 20, wherein the control exercised by said switch is initiation of operation of said occluder finger, said fluid moving finger, said pressure transducer, and said microprocessor upon cessation of introduction of the supplemental fluid.

23. The apparatus as recited in claim 20, wherein said switch is a pressure sensitive switch shaped to fit between the thumb of an operator and a plunger of a syringe being used to introduce the supplemental fluid.

24. A method of monitoring an intravenous fluid infusion procedure to test for a patency condition at the venous access site, comprising the steps of:

occluding an intravenous fluid infusion tube upstream from the venous access site;

manipulating an external surface of said tube to achieve a testing base pressure;

initiating a pressure drop in the fluid within said tube by manipulating said external surface of said tube;

sensing pressure in the fluid within said tube by contact with said external surface of said tube;

timing an interval between said pressure drop and a recovery of said pressure in the fluid to said testing base pressure;

comparing said time interval with a predetermined time limit; and displaying an alarm if said time interval is greater than said predetermined time limit.

25. The method as recited in claim 24, wherein said testing base pressure is about 0.5 psi below a stable pressure remaining in the fluid after occluding said tube.

26. The method as recited in claim 24, further comprising the steps of:

timing a second interval between occluding said tube and sensing a stable pressure in the fluid; and displaying an indicator of an unsatisfactory condition if said second time interval is greater than a second predetermined time limit.

27. The method as recited in claim 24, further comprising the steps of:
timing a second interval between manipulating said tube to achieve said testing base pressure and sensing said testing base pressure in the fluid; and
displaying an indicator of an unsatisfactory condition if said second time interval is greater than a second predetermined time limit.

28. The method as recited in claim 24, further comprising the steps of:
initiating a sequence of a plurality of pressure drops in the fluid, with each said drop followed by a recovery of pressure in the fluid to said testing base pressure;
timing a second interval for completion of said sequence; and
displaying an indicator of an unsatisfactory condition if said second time interval is greater than a second predetermined time limit.

* * * * *